US008785369B2

(12) United States Patent
Ford

(10) Patent No.: US 8,785,369 B2
(45) Date of Patent: *Jul. 22, 2014

(54) NEUREGULINS FOR PREVENTION AND TREATMENT OF DAMAGE FROM ACUTE ASSAULT ON VASCULAR AND NEURONAL TISSUE AND AS REGULATORS OF NEURONAL STEM CELL MIGRATION

(75) Inventor: Byron D. Ford, Atlanta, GA (US)

(73) Assignee: Morehouse School of Medicine, Atlanta, GA (US)

( * ) Notice: Subject to any disclaimer, the term of this patent is extended or adjusted under 35 U.S.C. 154(b) by 342 days.

This patent is subject to a terminal disclaimer.

(21) Appl. No.: 12/359,773

(22) Filed: Jan. 26, 2009

(65) Prior Publication Data

US 2009/0156500 A1 Jun. 18, 2009

Related U.S. Application Data

(62) Division of application No. 11/514,352, filed on Sep. 1, 2006.

(60) Provisional application No. 60/713,681, filed on Sep. 2, 2005.

(51) Int. Cl.
*A61K 38/00* (2006.01)
*C07K 14/00* (2006.01)
*A61K 38/17* (2006.01)

(52) U.S. Cl.
CPC .............. *A61K 38/17* (2013.01); *Y10S 977/915* (2013.01)
USPC ............................. 514/1.1; 530/350; 977/915

(58) Field of Classification Search
None
See application file for complete search history.

(56) References Cited

U.S. PATENT DOCUMENTS

| 6,087,323 | A | * | 7/2000 | Gwynne et al. ................ 514/8.4 |
| 6,252,051 | B1 | | 6/2001 | Godowski et al. |
| 6,635,249 | B1 | | 10/2003 | Marchionni et al. |
| 2004/0115175 | A1 | | 6/2004 | Blau et al. |

FOREIGN PATENT DOCUMENTS

WO 2005016966 A2 2/2005

OTHER PUBLICATIONS

Xu et al. (J Cereb Blood Flow Metab 26: 527-535, published online Aug. 31, 2005).*
Albers et al. (JAMA 283: 1145-1150, 2000).*
Xu et al. Biochem Biophys Res Comm 322: 440-446, published online Aug. 12, 2004.*
Shyu et al. (Neurobiol Aging 25: 935-944, Aug. 2004).*
Albers (Am J Cardiol. 80(4C): 4D-10D, 1997).*
Deer et al., Neuromod 10: 300-328, 2007—abstract.*
Anton, et al., "Role of GGF/neuregulin signaling in interactions between migrating neurons and radial glia in the developing cerebral cortex," Development, vol. 124, pp. 3501-3510 (1997).
Xu, et al., "Extended therapeutic window and functional recovery after intraarterial administration of neuregulin-1 after focal ischemic stroke," Journal of Cerebral Blood Flow & Metabolism, pp. 1-9 (2005).
Zhang, et al., "Neurotrophic and neuroprotective effects of the neuregulin glial growth factor-2 on dopaminergic neurons in rat primary midbrain cultures," Journal of Neurochemistry, vol. 91, pp. 1358-1368 (2004).
Xu, Zhenfeng et al., "Extended therapeutic window and functional recovery after intraarterial administration of recovery after intraarterial administration of neuregulin-1 after focal ischemic stroke", Journal of Cerebral Blood Flow & Metabolism (2006) 26, 527-535.
Ford, Gregory et al., "Expression Analysis Systematic Explorer (EASE) analysis reveals differential gene expression in permanent and transient focal stroke rat models", Brain Research 1071 (2006) 226-236.
Li, Yonggang et al., "Neuroprotection by neuregulin-1 in a rat model of permanent focal cerebral ischemia", Brain Research 1184 (2007) 277-283.

* cited by examiner

*Primary Examiner* — Daniel E Kolker
*Assistant Examiner* — Aditi Dutt
(74) *Attorney, Agent, or Firm* — Ping Wang; Andrews Kurth LLP

(57) ABSTRACT

Neuregulin, a known neuroprotein, has been found to ameliorate or prevent damage caused by mechanical or chemical assault to blood vessels and, when administered into the cerebral spinal fluid, can ameliorate damage to neuronal tissue caused by stroke or inflammation. Additionally, neuregulin has been found to be useful for enhancement of stem cell migration from the ventricle to the site of injury to the brain.

20 Claims, 2 Drawing Sheets

NEUREGULINS FOR PREVENTION AND TREATMENT OF DAMAGE FROM ACUTE ASSAULT ON VASCULAR AND NEURONAL TISSUE AND AS REGULATORS OF NEURONAL STEM CELL MIGRATION

This application is a divisional application of U.S. patent application Ser. No. 11/514,352, filed Sep. 1, 2006, which claims priority from Provisional Patent Application 60/713,681 filed Sep. 2, 2005. The entirety of all of the aforementioned applications is incorporated herein by reference.

This invention was partially supported by the United States Government NIH grant NS34194 and an NSF Center for Behavioral Neuroscience Cooperative Agreement (#IBN-9876754). Hence, the United States Government has certain rights in this invention.

FIELD

Background

This specification discloses novel means for treatment of acute vascular conditions which may arise from mechanical or chemical damage to the vascular system or that may arise from sudden decrease in blood supply to the brain, as occurs in obstructive stroke or damage to neuronal tissue that arises from neurotoxins by appropriate administration of neuregulin in accord with the teachings herein.

Neuregulins are a family of multipotent growth factors that includes acetylcholine receptor inducing activities (ARIAs), growth factors, heregulins, and neu differentiation factors. Neuregulins' effects appear to be mediated by interaction with a class of tyrosine kinase receptors related to the epidermal growth factor receptor. Neuregulins stimulate the tyrosine phosphorylation of these receptors and the subsequent activation of various signal transduction mechanisms. Neuregulins are synthesized as transmembrane precursors consisting of either an immunoglobuline-like or cysteine-rich domain, and EGF-like domain a transmembrane domain and acytoplastic tail. The EGF-like domain of NRG-1 appears to be sufficient for activation.

Neuregulin-1 (NRG-1) is expressed in vascular endothelial cells and its receptors are localized in the underlying smooth muscle cells. However, its use in treatment of acute conditions and for repair of damaged tissue by enhancing migration of stem cells to damaged areas to provide new neuronal tissue has not previously been disclosed.

Atherosclerosis is a major cause of death in Western civilizations, leading to both heart attack and strokes. Atherosclerosis is a complex, chronic inflammatory disease of the arterial vessel wall which involves multiple processes including endothelial dysfunction, inflammation, vascular smooth muscle cell (VSMC) proliferation, and matrix alteration. Damage to the endothelial lining of the arterial wall due to angioplasty, insertions of stents or catheters and atherosclerosis all induce the release of pro-inflammatory cytokines and growth factors that stimulate normally quiescent VSMC to migrate and proliferate. VSMC proliferate and migrate from the medial layer of the vessel into the intima resulting in neointimal hyperplasia, which is also a major cause of restenosis after angioplasty or cardiac surgery, especially surgery on the heart valves. Mitogens, such as platelet derived growth factor (PDGF), are potent stimulators of VSMC proliferation and differentiation following vascular injury. PDGF is produced by platelets, endothelial cells, smooth muscle cells and macrophages that infiltrate the artery in response injury and the release of PDGF after injury contributes significantly to the formation of the neointima.

Ischemic stroke occurs when the blood supply to the brain is obstructed. The neuronal death that ensues results from the induction of genes associated with a number of additional cellular functions. A substantial body of research implicates inflammation as a contributor to stroke morbidity. Ischemic stroke initiates an inflammatory response in the injured brain and progresses for days after the onset of symptoms. There is evidence that inflammatory reactions are involved in the delayed ischemic injury and result in poor prognosis of neurological outcome.

In response to cerebral ischemia, inflammatory cytokines, such as tumor necrosis factor (TNF$\alpha$) and interleukin-1$\beta$ (IL-1($\beta$), are induced in the ischemic brain of animal models. Following ischemic injury, IL-1$\beta$ and TNF$\alpha$, have been shown to facilitate neuronal damage. These cytokines induce the expression of adhesion molecules, downstream pro-inflammatory molecules and stress genes.

Chemical cause of neuronal damage include neurotoxins such as those used in chemical warfare and in some pesticides. Recent studies have demonstrated the existence of neuronal injury secondary to the stimulation of cholinergic pathways, which is associated with pro-inflammatory processes in the CNS following exposure to Organophosphorus (OP). OP nerve agents are toxic chemicals that have been used by terrorists in military combat and against civilian populations. Current post-exposure medical countermeasures against nerve agents (e.g. atropine, oximes and benzodiazepines) are useful in preventing mortality, but are not sufficiently effective in protecting the CNS from seizures and permanent injury. Therefore, new and more effective medical countermeasures to avoid post-exposure damage to neuronal tissues are needed. Recent studies have demonstrated the existence of neuronal injury, secondary to the stimulation of cholinergic pathways, which is associated with pro-inflammatory processes in the CNS following exposure to OP nerve agents.

The neuregulins have been known to be involved in the survival and function of neuronal cells. A recent study using NRG-1 demonstrated the neuregulin blocked delayed neuronal death following focal ischemic stroke. However, the mechanisms that underlie the neuroprotective effects of NRG-1 are unclear. Neurogenesis has been described in the adult mammalian CNS in the subventricular zone (SVZ) and dentate gyrus of the hippocampus. Studies have shown that neurogenesis may be stimulated from multiple cell types in the SVZ. Four cell types are found in the SVZ: neuroblasts (type A), SVZ astrocytes (type B), rapidly dividing precursors (type C), and multiciliated ependymal cells. Each type is capable of giving rise to neurons and glia.

Stem cells research has attracted widespread attention and controversy over the past several years. Stem cells are undifferentiated, primitive cells with the ability to differentiate into various kinds of cells. Stem cells can be used to restore or regenerate tissue, which could be useful in treating injuries or disease. Stem cell research is controversial because the best source of true pluripotent stem cells is human fetal tissue, which is harvested from destroyed embryos. Unlike embryonic stem cells, adult stem cells are unspecialized, undifferentiated cells that exist in very small numbers among specialized cells in an adult organ or tissue. Their main function is to maintain and periodically repair the tissues in which they are found. Adult stem cells are found in a number of locations, including the brain, the bone marrow, peripheral blood, blood vessels, skeletal muscle, skin, and liver. There is no controversy regarding the use of human adult stem cells in research, since they can be retrieved from the individual requiring the therapy.

Neurogenesis in the adult brain normally also occurs in two regions of the adult mammalian brain; the olfactory bulb and the dentate gyrus of the hippocampus. The neural stem cells (NSCs) destined for the olfactory bulb originate from the subventricular zone (SVZ), which lies along the length of the lateral ventricle. In the developing CNS, NSCs comprise a self-renewing cell population able to generate neurons, astrocytes and oligodendrocytes. The newly generated olfactory bulb NSCs proliferate and migrate in the SVZ along the rostral migratory stream (RMS) towards the olfactory bulb. These NSCs differentiate into two kinds of inhibitory interneurons in the olfactory bulb. Four cell types are found in the SVZ: neuroblasts (type A), SVZ astrocytes (type B), rapidly dividing precursors (type C), and multiciliated ependymal cells (EC) that line the ventricles. Focal clusters of rapidly dividing type C cells are found scattered along the RMS. The stem cells in the adult SVZ have been shown to be SVZ astrocytes in one study. SVZ astrocytes divide to give rise to rapidly dividing immature precursors (type C) that in turn generate the neurons that migrate to the olfactory bulb and differentiate into neuroblasts (type A). However, other reports suggest that EC may also serve as adult SVZ stem cells. New neurons in the hippocampus are derived from NSCs in the subgranular zone (SGZ) and give rise to granule cells that project to the CA3 region of the hippocampus. It has also been demonstrated that neurogenesis can occur in regions of the adult mammalian brain, like the neocortex, where it does not normally occur, via manipulation of endogenous multipotent precursors in situ.

NSCs of CNS are patterned in vivo to generate neurons, oligodendrocytes, and astrocytes. In vitro, pluripotent NSCs generate lineage-restricted, self-renewing neuron-restricted progenitors (NRPs), and glial-restricted progenitors (GRPs), which subsequently develop into fully differentiated neuron and glial cells, respectively. NRPs are mitotically active and electrically immature, and they express only a subset of neuronal markers. NRPs undergo additional changes to develop into mature, functional neurons. NSCs, NRPs, and GRPs have been previously isolated from mouse neural tubes that undergo self-renewal in defined medium, and differentiate into multiple neural phenotypes in mass culture. When isolated neuroepithelial NSCs are maintained in culture in the absence of a substrate that supports adhesion, cells form neurospheres. Neurospheres contain a relatively homogeneous population of NSCs that undergo self-renewal in response to either bFGF or EGF. It was observed, however, that after mitogen withdrawal, the NSCs were unable to undergo neuronal differentiation directly. These cells emerged from the neurosphere as NRPs. These NRPs were required to go through one or more rounds of cell division before neurogenesis could proceed to generate of neurons.

SUMMARY

Figure 1:
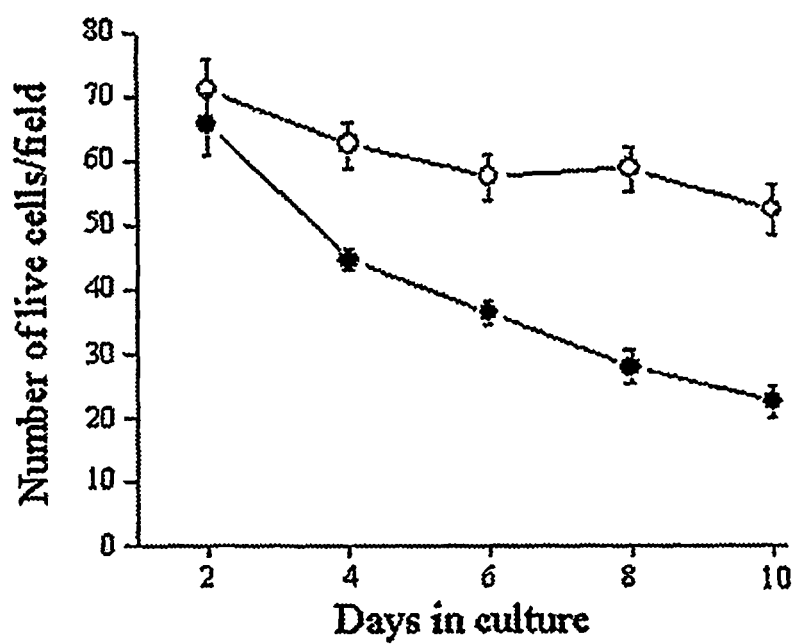
FIG. 1 is a diagram showing the effects of neuregulin-1 on PDGF-stimulated VSMC proliferation. The open cycles represent control cells. The filled cycles represent cells treated with neuregulin-1.
Figure 2:
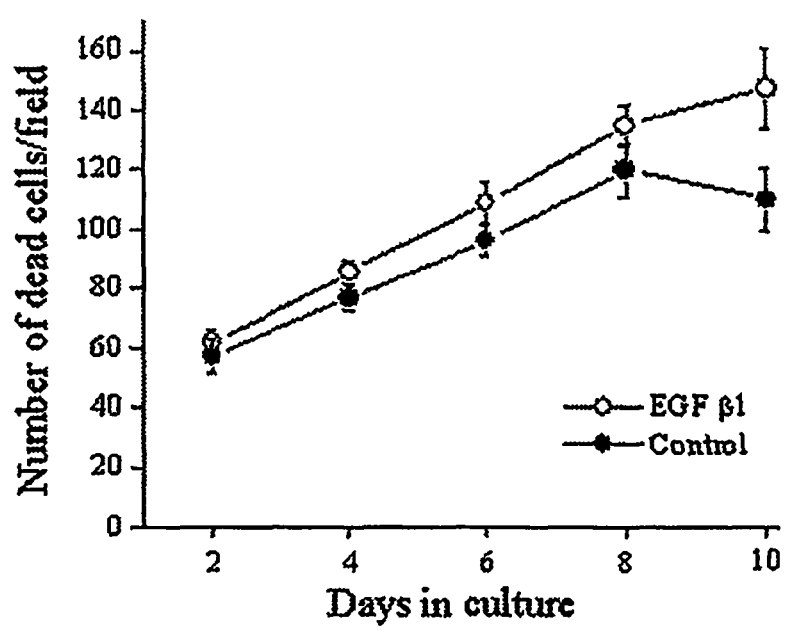
FIG. 2 is a diagram showing the effects of neuregulin-1 on NSCs isolated from E1 1 mouse telencephalon. The filled cycles represent control cells. The open cycles represent cells treatedwith the EGF-like domain of neuregulin-1β (EGF-1β).

It is the purpose of this invention to provide methods and compositions of neuregulins for use in treatment of persons who have suffered impairment of neuronal function due to destruction of neuronal cells by increasing migration of stem cells from the ventricle to the damaged areas of the brain. Intracerebro ventricular administration of neuregulin results in the mobilization and migration of endogenous NSCs in vivo. Results were shown when a subpopulation of these cells were studied when labeled with neuronal markers. Hence, neuregulins may be used as stimulators of adult neurogenesis and can be useful in treating neurodegenerative disorders, including stroke. The NSC-derived cells generated by NRG-1 are capable of repopulating regions of cell death following ischemic stroke. These findings may implicate a role for NRG-1 in neuronal regeneration following ischemic stroke, resulting in an increase in functional recovery following stroke.

It is a further purpose of this invention to provide methods and compositions for treatment of the acute phase (0-72 hours) of obstructive stroke by administration of neuregulin in conjunction with other treatment modalities such as glutamate receptor inhibitors which block the excitotoxic events of ischemia or t-PA, a clot disrupting agent, in order to decrease damage to neuronal tissue and injury arising because of reperfusion after administration of agents such as t-PA. The amelioration of neuronal damage is accomplished by administration of a inflammation inhibiting effective amount of neuregulin, in conjunction with the glutamate receptor inhibitor or a clot disrupting agent to a patient who has suffered an occlusive stroke, wherein the neuregulin is administered within 72 hours of the onset of said occlusive stroke.

Administration via the carotid artery within the treatment time window of up to 72 hours (therapeutic window) has not been disclosed previously. In order to access a particular portion of brain tissue in need of exposure, neuregulins can be administered to a particular area of tissue via fluoroscopy guided catheter in the usual manner used for catheter-based therapy. Neuregulin may also be administered intravenously in conjunction with reperfusion therapy following occlusion of coronary arteries.

It is a further purpose of this invention to provide protection from permanent neuronal damage after exposure to chemical damage such as that resulting from exposure to nerve poisons such as organophosphates.

It is a further purpose of this invention to provide protection from permanent damage to blood vessels from restenosis and artherosclerosis arising from physical assault such as placement of a balloon or stent in the artery or diagnostic procedures such as cardiac catheterization. Furthermore, restenosis may develop after cardiac surgery, especially surgery on the heart valves. In addition to administration of neuregulin by intravenous route during or after the damaging occasion, a stent or catheter for use in an invasive procedure may be coated with neuregulin.

In view of the above, the methods taught herein provide means of preventing damage from an acute assault on the neuronal and vascular tissue by appropriate, early treatment using neuregulins. Further treatment with neuregulins after damage has occurred may be achieved after the inflammatory phase following the acute onslaught by intrathecal administration of neuregulin to enhance proliferation of new cells in the damaged areas of the brain by increasing migration of stem cells to the damaged regions of the brain.

DETAILED DESCRIPTION

While it was previously shown that neuregulin-1 (NRG-1) increases the proliferation of neuronal restricted precursors (NRPs/type B cells) from cultures of embryonic neural stem cells (NSCs/type C cells). It is now found that neuregulins are mitogenic to NRPs. Hence, endogenous neuregulins play important roles during CNS neurogenesis. However, a specific role for neuregulins in the regulation of endogenous neurogenesis and its use in improving neuronal function by enhancing migration of stem cells by intrathecal administration of neuregulin has not been disclosed previously.

While there have been previous suggestions that neuregulin might have long term use in treatment of atherosclerotic conditions, its use in prevention or treatment of acute damage to the vascular system has not previously been disclosed. It has now been found that neuregulin also prevents mitogen-stimulated VSMC proliferation and migration. Hence, use of neuregulin represents a means of prevention of damage arising from response to invasive procedures.

To evaluate the potential role of neuregulin as an agent for use in vascular injury, the effect of NRG-1 on neointimal formation following balloon injury to the carotid artery of the rat was examined. NRG-1 (2.5 ng/kg) was administered by tail-vein injection prior to injury and every two days following injury. Two weeks after carotid artery injury, NRG-1-treated animals demonstrated a 50% reduction in lesion size compared to controls receiving the vehicle. To examine possible mechanisms for NRG-1 action, its effect on vascular smooth muscle cell (VSMC) function was studied. A7r5 rat VSMC cultures were pretreated with NRG-1 for 24 hours, and then stimulated with platelet derived growth factor (PDGF) for 48 hours. NRG-1 significantly decreased both baseline and PDGF-stimulated VSMC proliferation in a dose-dependent manner. NRG-1 also blocked VSMC migration and prevented the downregulation of a-smooth muscle actin by PDGF, indicating that it may prevent VSMC phenotypic reversion following injury. These findings demonstrate NRG-1 as be a novel therapeutic agent for the treatment of restenosis and atherosclerosis.

Methods in Study of Prevention of Post-Trauma Damage to Blood Vessels: Experimental Injury, Harvest, and Tissue Preparation of Rat Carotid Arteries Male Sprague-Dawley rats (350-400 g) were balloon-injured using methods as previously described in accordance with a protocol approved by the Standing Committee on Animals, Morehouse School of Medicine. Rats were anesthetized with an intraperitoneal injection of xylazine (5 mg/kg body weight) and ketamine hydrochloride (90 mg/kg body weight). The left common carotid artery was exposed by a 6-cm midline cervical incision. Proximal and distal blood flow was occluded by clamping. Polyethylene 10 tubing was inserted retrogradely into the internal carotid artery and advanced into the left common carotid artery. After gentle flushing of the artery with normal saline, the tubing was removed and a 2-French (F) Fogarty embolectomy balloon catheter was inserted. Balloon inflation to 1.5 to 1.8 times the external diameter of the artery was achieved by caliper measurement under stereomicroscopy. After holding the inflation for 30 seconds, the catheter was removed. The uninjured right carotid artery was used as the control. Rats were treated with NRG-1β or NRG-1α (EGF-like domain, R&D Systems, Minneapolis, Minn. dissolved in 1% BSA/PBS) by tail-vein administration at a dose of 2.5 ng/kg body weight, starting at day 0 before injury, and continuing for every 2 days for the next 14 days. Control rats were treated with vehicle (1% BSA/PBS). The animals were weighed before the procedure and at sacrifice to evaluate the possible adverse effects of NRG-1. Vessels were harvested time points 0 and 14 days for mRNA analysis or histology. Injured vessels were compared with their contralateral controls.

Tissue Processing and Quantitative Histomorphometric Analysis

Animals were euthanized with $CO_2$ 14 days after injury. Carotid arteries were washed with saline to clear blood, embedded in Tissue-Tek OCT medium and frozen using liquid nitrogen. Carotid sections were cut with a cryostat into cross sections of 12 μm taken from the center and distal portion of the vessels, and stained with hematoxylin and eosin. The medial thickness was determined by the area of the internal elastic lamina subtracted from the external elastic lamina. Morphometry was performed using at least six individual sections of each arterial segment and used to determine the lesion size expressed as intima/media ratio. The intimal and medial layer thicknesses were measured using a computer-based image analyzing program (Image J, NIH).

A7r5 VSMC Cultures

A7r5 rat aortic vascular smooth muscle cells (VSMC) (ATCC CRL-1444) were obtained from American Tissue Type Culture (Manassas, Va.) and grown in Dulbecco's modified Eagle medium supplemented with glutamine, 10% fetal calf serum (FCS), and 1% Penicillin/Streptomycin at 37° C. in a humidified incubator with 5% $CO_2$. Cells were passaged weekly. All studies were performed on cells from passages 9-12.

Determination of VSMC Proliferation

VSMC were seeded at a density of $1 \times 10^3$ cells in triplicate wells of a 96 well plate. After 24 hours, cells were serum starved in DMEM/F-12 (Gibco; Carlsbad, Calif.) containing 0.1% FCS (low serum medium; LSM) to induce quiescence. After 24 hours of serum deprivation, cells were pretreated with 0-200 nM of NRG-1α or NRG-1β for 24 hours. Cells were then treated with 10 ng/mL of PDGF-BB for 48 hours to stimulate VSMC proliferation. For direct measure of cell number, cells were counted using a Coulter counter. VSMC cell proliferation and viability was also measured using the CellTiter 96 AQueous Non Radioactive Cell Proliferation Assay (Promega; Madison, Wis.) according to the manufacturer's protocol. After incubation at 37° C. in humidified 5% $CO_2$ for 1 hour, the absorbance was recorded at 490 nm using a plate reader. Measurement of DNA synthesis was performed using the BrDU Cell Proliferation Assay (Calbiochem, San Diego, Calif.) according to the manufacturer's protocol.

Cell Migration Assay

Neuro Probe 48-well microchemotaxis chambers (Costar, Corning Inc.) with PVP-free polycarbonate filter (8.0 μm pore size) were used to measure VSMC migration. Quiescent cells were trypsinized and resuspended in LSM with or without NRG-1 and incubated for 24 hours at 37° C. Cells were then treated with PDGF which was added to the bottom well of the Boyden chamber and incubated for 48 hours at 37° C. Cells that migrated to the lower side of the filters were fixed and stained with the Diff Quick staining kit (VWR Laboratory, West Chester, Pa.). The filters were mounted on glass slides and counted by light microscopy using ×100 magnification.

Protein Purification and Western Analysis

Reactions were terminated by placing the cells on ice, aspirating the medium and adding ice-cold lysis buffer (50 mM Tris, 150 mM NaCl, 1mM EDTA, 0.5% Triton X-100, 0.5% Nonidet P-40, 1 mM sodium orthovanadate, 1 mM phenyl methanesulfonyl fluoride, pH 8.0) for 30 minutes at 4° C. Harvested lysates were denatured with loading buffer, resolved in SDS/5% polyacrylamide gels and transferred to poly vinylidene difluoride (PVDF) membranes (Millipore Corp., Bedford, Mass.). Membranes were be blocked with 3% nonfat dry milk in phosphate buffered saline-0.5% Tween 20 (PBST) and exposed to primary antibody, anti-smooth muscle alpha-actin (SMA) (Santa Cruz, Calif.) diluted in blocking buffer overnight at 4° C. After incubation, membranes were washed with PBST. After wash, membranes were exposed to an alkaline phosphatase-conjugated anti-rabbit secondary antibody for 1 hour. Membranes were subsequently washed with PBST, incubated with chemiluminescence reagents and exposed to x-ray film. For ERK1/2 phosphorylation, VSMC were pre-treated with NRG-1β for 24 hours and stimulated for 15 minutes with PDGF. Western blots were performed using primary antibodies for phosphorylated and unphosphorylated forms of ERK1/2 (Cell Signaling, Danvers, Mass.) diluted 1:250 in blocking buffer. Immunoblotting using an anti-tubulin antibody was used to normalize protein levels in each sample.

Cell Viability Assay

Quantitative viability assessment was performed using 1% Calcein-AM (Molecular Probes, Eugene, Oreg.), a fluorescent membrane-integrity dye, diluted in HBSS according to the manufacturer's protocol. Qualitative assessment of cell viability in treated cells was performed using the trypan blue-exclusion assay. Non-viable viable cells were quantified visually using a light microscopy.

Statistical Analysis

Each experiment was repeated a minimum of three times. Data are expressed as the mean±standard deviation (SD). An unpaired Student's t-test and ANOVA were performed to make comparisons between groups. A value of p less than 0.05 was considered significant.

Results

NRG-1 Attenuated Neointima Formation After Rat Carotid Balloon Injury

Neointimal hyperplasia was histologically evident in the carotid arteries 14 days after balloon injury compared to uninjured contralateral controls. The neointima of the rats receiving intravenous administration of NRG-1 was significantly reduced compared to balloon-injured animals. Morphometric analysis showed that NRG-1 reduced the size of the lesion by 50% compared to vehicle-treated control animals. Treatment of animals with NRG-1 showed no overt negative side effects and there was no significant difference in body weight observed among the control and NRG-1 treated rats.

NRG-1 Inhibits Proliferation in VSMC

One possible mechanism for the inhibitory effect of NRG-1 on neointimal formation is the regulation of pathological VSMC functions. To examine the effects of NRG-1 on VSMC proliferation, serum-starved VSMC were pre-treated with NRG-1 for 24 hours, then stimulated with PDGF for an additional 48 hours. Stimulation of cells with PDGF increased proliferation of VSMC 2-fold. Pre-treatment with either NRG-1β (FIG. 1a) or NRG-1a resulted in a dose-dependent decrease in baseline and PDGF-stimulated proliferation as measured by MTS activity. Direct cell counting using Coulter counter demonstrated that NRG-1 reduced PDGF-stimulated VSMC proliferation, but not baseline cell numbers. Analysis of BrDU incorporation revealed a similar pattern to the Coulter counter demonstrating that NRG-1β significantly inhibited PDGF-induced proliferation, but did not alter baseline DNA synthesis.

To determine whether the growth inhibitory effects of NRG-1 were due to toxicity or damage to the cells rather than proliferation, calcein-AM and trypan blue viability assays were carried out in cells pre-treated with NRG-1 with or without PDGF. The calcein-AM assay demonstrated that treatment of VSMC with NRG-1 does not alter cell viability. These results were corroborated using the trypan-exclusion assay, which revealed that less than 1.0% of the cells took up the dye.

NRG-1 Decreases VSMC Migration

The migration of VSMC was measured using a transwell migration assay. VSMC were pretreated with 100 nM NRG-1α or NRG-1β, and then stimulated with 10 ng/ml of PDGF-BB for 48 hours. Our results show that NRG-1 alone does not alter baseline VSMC migration. VSMC treated with PDGF displayed a 2-3 fold increase in migration. Both NRG-1α and NRG-1β decreased PDGF-stimulated VSMC migration by 80% and 90%, respectively.

NRG-1 Regulates Smooth Muscle α-Actin Expression

To examine the possibility that NRG-1 may block VSMC proliferation and migration by preventing de-differentiation, the mRNA and protein expression on SMA, a marker for differentiated and contractile VSMC, after NRG-1 treatment was examined. Serum-starved, quiescent VSMC displayed SMA expression, which was reduced after treatment with PDGF. NRG-1β alone did not alter SMA mRNA or protein expression, however, pre-treatment of PDGF-stimulated VSMC with NRG-1β resulted in SMA expression that returned to near baseline levels.

NRG-1 Inhibits PDGF-Induced Phosphorylation of ERK1/2

Several studies have shown that PDGF-induced VSMC proliferation involves the ERK, signaling pathway. Regulation of the phosphorylation of these kinases was used to determine whether NRG-1 could inhibit PDGF activity in VSMC by interfering with ERK activity. PDGF stimulation of VSMC resulted in an induction of ERK1/2 phosphorylation. Treatment with NRG-1 alone did not alter ERK1/2 phosphorylation compared to control untreated VSMC. However, NRG-1 prevented PDGF-induced phosphorylation of ERK 1/2. Densitometric revealed that NRG-1 reduced PDGF-stimulated ERK1/2 phosphorylation in VSMC by 70%.

While the NRG-1/erbB system had previously been shown to modulate various biological activities including cell survival, proliferation, and migration, which are critical for normal development and pathology in a variety of tissues, the role for NRG-1 in vascular function and injury has not been clearly elucidated. This study, demonstrated that NRG-1 attenuates neointimal formation and vascular balloon injury. NRG-1 reduced the size of the lesion by 50% compared to vehicle-treated control animals. This novel finding clearly shows that NRG-1 is useful in the prevention of vascular diseases such as restenosis and atherosclerosis. The NRG-1 blocks PDGF-induced proliferation of VSMC in a dose-dependent manner. The inhibitory effects of NRG-1 on VSMC proliferation were confirmed by direct cell counting and measuring DNA synthesis by BrDU incorporation. An intriguing observation was the difference in the effect of NRG-1 on baseline VSMC proliferation using the MTS-based assay compared to the other methods. In the cell counting and BrDU approaches, PDGF increased VSMC proliferation was blocked by NRG-1, however, baseline VSMC numbers were not altered. Using the MTS-based assay, a 50% decrease in baseline MTS activity was seen after NRG-1 administration. Since the MTS assay measures metabolic activity, it is possible that NRG-1 may prevent PDGF-stimulated proliferation by promoting VSMC differentiation, which could result in a decrease in metabolic activity and/or a reduction in the capability of PDGF to stimulate VSMC proliferation. That this is due to apoptosis resulting from treatment is unlikely since there was no evidence of increased dead or non-viable cells after neuregulin treatment.

Combination Therapy to Prevent Permanent Neuronal Damage

In the case of prevention of damage resulting from exposure to neurotoxins such as organophosphates or as a result of obstructive stroke such as that caused by an infarct studies were done studying effect on permanent middle cerebral artery occlusion (pMCAO) using combination therapy. Studies were done giving dizocilpin maleate (MK-801 from Sigma), a glutamate receptor inhibitor which blocks the excitotoxic events of ischemia in combination with neuregulin within a therapeutic window of about 13.5 hours in the rat to decrease permanent neuronal damage. The therapeutic window in larger animals having a lower metabolism would be in the range of 0 to 72 yours. In the case of expected exposure to neurotoxins, the neuregulin could be administered in conjunction with antidotes. Other active agents which may be used in conjunction with neuregulin in the manner disclosed for use with MK-801 are selfotel, aptiganel, magnesium, acetylcholine, GABA agonists (clomethiazole, diazepam and other benzodiazepines) and serotonin agonists.

In the case of damage arising from exposure to neurotoxins current post-exposure medical countermeasures against nerve agents (e.g. atropine, prostigmine glutamate antagonists, oximes (such as 20 pralidoxime chloride) and benzodiazepines) are useful in preventing mortality, but are not sufficiently effective in protecting the CNS from seizures and permanent injury. Therefore, new and more effective medical countermeasures against OP nerve agents are needed to facilitate better treatment that will prevent extensive, permanent nerve damage in survivors. Other agents that may be used to treat patients that have been exposed to neurotoxin include anticonvulsants.

In both instances of pMCAO and exposure to neurotoxins, the neuregulin may be administered concurrently with the other active agents to ameliorate permanent damage from infarct disintegrators or nerve agent counteractants, but should be given within a 72 hour widow after the initial exposure to the causative agent or the onset of occlusion of the blood supply, more preferably within 24 hours after the causal event.

In both instances where the neuregulin is given as combination therapy to prevent cerebral neuronal damage the neuregulin is administered into the carotid artery with an appropriate carrier. In animal studies, the neuregulin is administered in bovine serum albumin. In humans, a preferred carrier would be human serum to be administered within the first 72 hours, preferably within the first 24 hours, of the assault, whether chemical or physical. (In the instance where the neuregulin is to prevent damage resulting from mechanical damage to a blood vessel, the neuregulin may be given intravenously in the usual carriers used for intravenous administration.

Addressing the use of neuregulin simultaneously with other agents, studies were done on rats that had been subjected to left middle cerebral artery occlusion (MCAO).

Methods

Middle Cerebral Artery Occlusion

All surgical procedures were performed by sterile/aseptic techniques in accordance with institutional guidelines. Adult male Sprague-Dawley rats weighing 250-300 g were used for this study. Animals were subjected to left MCA occlusion. Rats were anesthetized with a ketamine/xylazine solution (10 mg/kg, IP). MCA occlusion was induced by the intraluminal suture MCAO method as previously described (Belayev et al. 1996; Belayev et al. 1995). Briefly, the left common carotid artery (CCA) was exposed through a midline incision and was carefully dissected free from surrounding nerves and fascia. The occipital artery branches of the external carotid artery (ECA) were then isolated, and the occipital artery and superior thyroid artery branches of the ECA were coagulated. The ECA was dissected further distally. The internal carotid artery (ICA) was isolated and carefully separated from the adjacent vagus nerve, and the pterygopalatine artery was ligated close to its origin with a 6-0 silk suture. Then, a 40 mm 3-0 surgical mono filament nylon suture (Harvard Apparatus, Holliston, Mass.) was coated with poly-L-lysine with its tip rounded by heating near a flame. The filament was inserted from the external carotid artery (ECA) into the internal carotid artery (ICA) and then into the circle of Willis to occlude the origin of the left middle cerebral artery. The suture was inserted 18 to 20 mm from the bifurcation of the CCA to occlude the MCA. In the permanent MCAO (pMCAO), the suture was left in place for 24 hours prior to sacrificing the animal. In the transient MCAO (tMCAO) model, the nylon suture was withdrawn 1.5 hours following ischemia and the brain tissues were reperfused for 24 hours before sacrificing. To determine the effects of NRG-1 on ischemic stroke, rat were injected intra-arterially with a single bolus 10 ul dose of vehicle (1% BSA in PBS) or NRG-1β (10 nmol/L NRG-1 (EGF-like domain, R&D Systems, Minneapolis, Minn.) in 1% BSA in PBS) through a Hamilton syringe. This resulted in the administration of ~2.5 ng of NRG-1/kg body weight. NRG-1 or vehicle was administered by bolus injection into the ICA through ECA immediately before MCAO. MK-801 (0.5 mg/kg) was either administered IP immediately prior to NRG-1 administration or co-administered IA simultaneously with NRG-1. All NRG-1 and vehicle treatment studies were performed in a double-blinded manner. Core body temperature was monitored with a rectal probe and maintained at 37° C. with a Homeothermic Blanket Control Unit (Harvard Apparatus) during anesthesia. Neurological score was determined in a double blinded fashion using a five-point neurological evaluation scale (Menzies et al. 1992) in rats treated with vehicle or NRG-1 four hours after reperfusion. All animals were tested prior to surgery (controls) and after treatment with NRG-1 or vehicle. Neurological function was graded on a scale of 0-4 (normal score 0, maximal deficit score 4). While intra-arterial injection into the carotid artery was used, fluoroscopic guided catheter-based therapy wherein the catheter is guided to the arteries which best access the damaged tissue is appropriate.

Measurement of Infarct Formation

Twenty-four hours after reperfusion, the animals were killed and the brain tissue was removed and sliced into 2.0 mm-thick sections. Brain slices were incubated in a 2% triphenyltetrazolium chloride (TTC) solution for 30 minutes at 3° C. and then transferred into a 4% formaldehyde solution for fixation. TTC, a colorless salt, is reduced to form an insoluble red formazan product in the presence of a functioning mitochondrial electron transport chain. Thus, the infarcted region lacks staining and appears white, whereas the normal non-infarcted tissue appears red. Infarct area of four slices of 2 mm coronal sections of each brain was calculated in a blinded manner by capturing the images with a digital camera. Rats showing tremor and seizure (which rarely occurred in this study) were excluded from studies of brain infarction to eliminate cerebral hemorrhage or brain trauma as potential variables in this study. Infarct volumes were analyzed by ANOVA; $P<0.05$ was regarded as significant.

While it had previously been demonstrated that a single 2.5 ng/kg intra-arterial administration of NRG-1 prior to MCAO prevented neuronal death following ischemia and reperfusion, there was no indication that use at or after time of assault, whether mechanical (as with an infact) or chemical, would be effective to ameliorate damage arising from the assault.

Neuregulin also has use, with similar dosage for intravenous administration in conjunction with reperfusion therapy such as anticoagulant therapy to ameliorate damage to the artery. In such instances, the neuregulin may be administered in carriers such as glucose, saline, Ringer's lactate, etc.

Agents with other mechanisms of action that prevent or avoid formation of obstructive occlusion such as those which cause clots to dissolve can be used with neuregulin. Tissue plasminogen activator (t-PA) can also be used in conjunction with neuregulin. At present, use of t-PA remains limited and must be administered within three hours of the observed ischemic event. However, t-PA patients are at high risk of hemorrhagic transformation. Furthermore, t-PA causes inflammatory responses and reperfusion injury in the brain. The t-PA is administered intravenously in saline or similar carriers. In all instances, the neuregulin is most effective if administered into the carotid artery in a carrier containing serum albumin (in the case of humans, human serum albumin). The agents may be administered essentially simultaneously or the neuregulin may be administered within the 0-72 hour time period, though it is preferred practice to administer the neuregulin within 24 hours of administration of the t-PA.

Intrathecal Use of Neuregulin to Encourage Migration of Stem Cells for Proliferation of New Neuronal Cells While treatments cited above may be effective in limiting damage from a pathology-causing event, the recovery of function can take place only with regeneration of neuronal tissue. The administration of neuregulin into the ventricular zone provides means for enhancing migration of stem cells which are formed in the ventricle to the site of neuronal damage The Effect of NRG-1 on NSCs Isolated from E11 Mouse Telencephalon To investigate the effects of NRG-1 in multipotent NSCs, the telencephalon of E1 1 mouse embryos were isolated and the dissociated cells cultured as neurosphere cultures. In the present study, cultures were treated with the EGF-like domain of neuregulin-1β (NRG-1). The EGF-like domain contains the receptor binding portion of the molecule and has been shown to display all the known biological activities of the full-length neuregulins. The cells formed neurospheres and expressed nestin, an intermediate filament protein present in NSCs and RPs in the developing CNS. The cultures were examined to determine whether the addition of NRG-1 to cell suspensions obtained from E1 1 mouse cortical tissue would generate neurospheres in the absence of bFGF. After 7 days in culture, there was no significant difference in the total number or size of neurospheres in the NRG-1 treated group compared with the untreated group, This result demonstrated that NRG-1 alone, unlike bFGF, could not generate neurospheres. When bFGF-generated neurospheres were plated onto coated coverslips in the presence of bFGF, cells continued to divide and migrate out of the sphere to form a monolayer. Upon withdrawal of bFGF, migrating cells differentiated into cells expressing neuronal, astrocyte and oligodendrocyte markers. Neuronal cells were identified by labeling with the anti-MAP2 antibody. Oligodendrocytes were identified with an antibody directed against 04 and astrocytes were identified with an antibody directed against GFAP. Morphologically, these MAP2-positive cells appeared neuronal and showed: (i) a spherical, ovoid, or pyramidal shaped soma; (ii) phase-bright appearance; (iii) branching processes (presumably dendrites) arising from the soma.

NRG-1 Increases the Proliferation of MAP2-Positive Cells in Neurosphere Cultures The actions of NRG-1 on bFGF-generated neurospheres were examined by plating neurospheres on coverslips as described above. Neurospheres were cultured in the absence or presence of 5 nM NRG-1 for 5 days, and then co-labeled with BrDU and MAP2 or GFAP antibodies. After 5 days of treatment with 5 nM NRG-1, a dramatic increase in the number of cells surrounding the core of the neurosphere was observed in NRG-1 treated cultures as compared to control. A 44±3.3% increase in [3H]thymidine incorporation was seen in NRG-1 treated cultures that paralleled the increase in the total number of cells. More MAP2 and BrDU co-labeled cells (yellow) were found both in the central core and peripheral area of NRG-1 treated neurospheres, but few double-labeled cells were seen in the control. There was a 2.5-fold increase in MAP2 positive cells, but no increase in MAP2-negative cells, suggesting that the majority of NRG-1 treated cultures were neuronal.

To further characterize the effect of NRG-1 on NSCs, neurospheres were cultured in the absence or presence of 1 or 5 nM NRG-1, then co-labeled with BrDU and MAP2 or GFAP antibodies. After 5 days, there was a 4-fold increase in the number BrDU-labeled cells in the neurosphere outgrowth area in 5 nM NRG-1 treated group compared to control. A smaller, but significant increase was also observed with 1 nM NRG-1 treatment demonstrating a dose-dependent response of cells to NRG-1. Most of the BrDU positive cells co-labeled with the MAP2 (red, 3b), but not the GFAP antibody. Therefore, the increased proliferation was specific for neuronal cells and not in GFAP-positive astrocytes. The increase in number of MAP2 positive cells that co-labeled with BrDU was parallel to the increase of BrDU positive cells, suggesting that most of the cells proliferating in response to NRG-1 were neuronal. In cultures maintained for 8 days after withdrawal of bFGF, virtually no cells showed BrDU incorporation in control cultures. By that time point, most cells had differentiated and lost the ability to proliferate. However, numerous BrDU-positive neurons were present in the NRG-1 treated group, suggesting that NRG-1 prolongs the proliferation of immature neuronal cells (data not shown). Under our culture conditions, few cells were labeled with GFAP and O4 in control cultures, or after treatment with NRG-1, therefore the cells that labeled with BrDU alone were likely undifferentiated NSCs.

NRG-1 Increases Proliferation Rather Than Survival

The increased production of neurons could be altered by affecting (1) the proliferation of NRPs (2) the differentiation of NSCs into neurons, or (3) or by altering the survival of neuronal cells. Increased proliferation might result in an increase in the total number of cells as well as in the number of proliferating MAP2-positive cells; increased differentiation might result in an increase in the number of MAP2-positive cells within the same total population of cells; increased survival might result in an increase in MAP2-positive cells, but not necessarily cells co-labeled with BrDU or nestin. To determine whether the increase in the number of NRPs induced by NRG-1 was due to the increase of cell survival, we evaluated cell viability by using a Viability. Assay Kit (Molecular probes). Results showed that the total number of cells increased after 4 days in the cultures. The number of live cells was greater in NRG-1 treated group compared to control. Twice as many live cells were present in the NRG-1 group after 8 days. There was no difference in the number. If dead cells in control or NRG-1 treated cultures at most time points. This result shows that NRG-1 stimulated proliferation rather than cell survival.

NRG-1 Stimulates the Mobilization of NSCs in Adult Rat Brain In Vivo.

To examine whether NRG-1 could stimulate neurogenesis in vivo, we labeled. SVZ cells by stereotaxically injecting DiI into the lateral ventricle. Twenty-four hours later, NRG-1 or vehicle were injected into the lateral ventricle and sacrificed animals 1 day later. Intense labeling was visible in the cells lining the ventricle (V) and in the choroids plexus (CP) after injection of DiI. When the vehicle was injected 24 after the DiI labeling, few cells had migrated out from the SVZ. However, after NRG-1 administration, numerous NSCs had migrated from the SVZ, as far away as to the cerebral cortex. Similar results were seen when Fluorogold was injected into the lateral ventricle. Preliminary results indicate that a subpopulation of the labeled cells co-label with an antibody for NeuN, a neuronal marker (not shown).

The poor regenerative capacity of the sensory of the mammalian CNS has led to investigations of different approaches to increase the function of these structures after neurodegeneration or injury. One strategy to repair the injured CNS has been to replace the lost neurons with embryonic stem cell-derived neuronal stem cells (eNSCs). The use of eNSCs has shown promise in the treatment of a variety of neurological diseases and they have recently been shown to survive and differentiate into glia and neurons after CNS transplantation. However, a number of biological and ethical issues have slowed this area of research. NSCs have been demonstrated in the adult brain and have been shown to have the potential to differentiate into a variety of neuronal cell types. Therefore, another strategy has focused on maximizing the potential of this endogenous population of cells by stimulating their mobilization, proliferation, migration, and differentiation in vivo following CNS injury and degeneration. Understanding the technical and logistic considerations for employing adult NSCs is essential to optimizing and maintaining cell survival before and after activation, as well as for tracking the fate of mobilized cells. It is now recognized that NSC strategies will be effective only if the new cells have the same abilities and characteristics as the original neurons. Before the full potential of adult NSCs can be recognized for treating CNS injury, we must to identify the sources of stem cells, understand factors that can regulate their proliferation, fate specification, and, most importantly, to characterize their functional properties.

The administration of NRG-1 into the cerebral spinal fluid or through a shunt into the ventricle for repeated administration (intrathecal administration) gives a method of encouraging production of stem cells in the ventricle with migration of stem cells from the ventricle to the damaged areas of the brain. Administration may be used with spinal tap or may be administered through a shunt into the ventricle. Appropriate carriers include glucose, isotonic glucose and other carriers usually used for intrathecal administration. Dosage will vary with the size and condition of the animal, with range of 0.005 to 3 ng/Kg, with dosage of about 0.005 to 0.5 ng/Kg being administered to larger mammals. However, the neuregulin may be administered into the cerebral spinal fluid at the lumbar region. Dosage compositions would contain 0.05 to 100 ng in a pharmaceutically acceptable carrier. For arterial administration, the carrier may, advantageously, contain serum albumin.

When administered in conjunction with another active agent such as an antidote to a neurotoxin, an agent to dissolve clots or interfere with clot formation or some other active agent, such agents will be given in the manner usual for administration of such agent, often intravenously. However, to obtain maximum benefit, the neuregulin will usually administer into the carotid artery or by some other means such as fluoroscopy guided catheter-based means that will provide arterial access to the brain.

The use of shunts into the ventricle is well established practice in the medical community. Such shunts may be present for several day or weeks. While usually used to drain excess cerebral spinal fluid from the ventricle in cases of excessive production or blockage of flow, such shunts would be appropriate means for administration of neuregulin over a period of several weeks. The care of the shunt would be an ongoing responsibility of the medical team during the time neuregulin is being administered to facilitate migration of the stem cells to areas of damage.

For purposes of regeneration of neuronal tissue, the administration of NRG-1 should commence after the initial inflammation due to the assault has subsided. Because it is necessary for the stem cells that have migrated to be replenished in the ventricle, the intrathecal administration of neuregulin should not be repeated at less than one week intervals. Longer intervals may be appropriate in order to allow greater replenishment of the stem cell supply in the ventricle.

While NRG-1 has been exemplified, neuregulins 2, 3, and 4 have been shown to have similar activity and would also be appropriate for uses taught herein.

What is claimed is:

1. A method for ameliorating occlusive stroke damage in a patient by increasing migration of neural stem cells to damaged areas of the brain, comprising the step of:
    administering an effective neural stem cell migration-inducing and inflammation inhibiting amount of neuregulin-1 to a patient who has suffered an occlusive stroke, wherein said neuregulin-1 is administered within about 13.5 to 72 hours after the onset of said occlusive stroke.

2. The method of claim 1, wherein said neuregulin-1 is administered with a carrier, and wherein the carrier is serum albumin.

3. The method of claim 2, wherein said serum albumin is human serum albumin.

4. The method of claim 1, wherein the dosage of neuregulin-1 administered is 0.05 to 100 ng/kg.

5. The method of claim 1, wherein the dosage of neuregulin-1 administered is 0.05 to 5 ng/kg.

6. The method of claim 1, wherein said patient is additionally administered with tissue plasminogen activator (t-PA).

7. The method of claim 1, wherein said patient is additionally administered with a glutamate receptor inhibitor.

8. The method of claim 7, wherein said glutamate receptor inhibitor is dizocilpin maleate.

9. The method of claim 1, wherein said neuregulin-1 is administered into the cerebral spinal fluid of said patient by injection at the lumbar region.

10. The method of claim 1, wherein said neuregulin-1 is administered via an intrathecal route.

11. The method of claim 1, wherein said neuregulin is administered via a shunt into the ventricle or subventricular zone.

12. The method of claim 1, wherein said neuregulin-1 is administered intravenously or intra-arterially.

13. The method of claim 1, wherein said neuregulin-1 is administered into the carotid artery.

14. The method of claim 1, wherein said neuregulin-1 is administered within about 13.5 to 24 hours after the onset of said occlusive stroke.

15. The method of claim 1, wherein said neuregulin-1 is administered within 24-72 hours after the onset of said occlusive stroke.

16. A method for ameliorating occlusive stroke damage in a patient, comprising:

administering an effective amount of neuregulin-1 to a patient who has suffered an occlusive stroke, wherein said neuregulin-1 is administered within about 13.5 to 72 hours after the onset of said occlusive stroke.

17. The method of claim 16, wherein said patient is additionally administered with tissue plasminogen activator (t-PA).

18. The method of claim 16, wherein said neuregulin-1 is administered intravenously, intraarterially or intrathecally.

19. The method of claim 16, wherein said neuregulin-1 is administered within about 13.5 to 24 hours after the onset of said occlusive stroke.

20. The method of claim 16, wherein said neuregulin-1 is administered within 24-72 hours after the onset of said occlusive stroke.

* * * * *